(12) United States Patent
Kazes

(10) Patent No.: US 8,960,206 B2
(45) Date of Patent: Feb. 24, 2015

(54) FLOSSING DEVICE

(76) Inventor: Erez Benn Kazes, Herzliya (IL)

( * ) Notice: Subject to any disclaimer, the term of this patent is extended or adjusted under 35 U.S.C. 154(b) by 0 days.

(21) Appl. No.: 13/323,896

(22) Filed: Dec. 13, 2011

(65) Prior Publication Data

US 2012/0080050 A1 Apr. 5, 2012

Related U.S. Application Data

(63) Continuation-in-part of application No. 12/666,708, filed as application No. PCT/IL2008/000881 on Jun. 26, 2008, now abandoned.

(60) Provisional application No. 60/946,732, filed on Jun. 28, 2007.

(51) Int. Cl.
*A61C 15/00* (2006.01)
*A61C 15/04* (2006.01)
*A61C 15/02* (2006.01)

(52) U.S. Cl.
CPC .............. *A61C 15/046* (2013.01); *A61C 15/00* (2013.01); *A61C 15/02* (2013.01); *A61C 15/042* (2013.01)
USPC ......................................... 132/329; 132/321

(58) Field of Classification Search
CPC ........ A61C 15/00; A61C 15/02; A61C 15/04; A61C 15/041; A61C 15/042; A61C 15/045; A61C 15/046
USPC ......... 132/321, 200, 309, 320, 323, 324, 329; 132/325, 326, 327, 328, 322; 433/143, 148, 433/149, 39; 424/49, 52; 427/2.29; 428/364, 371, 377; 57/201, 21; 606/148, 150, 225; D28/65, 66, 67, 68
See application file for complete search history.

(56) References Cited

U.S. PATENT DOCUMENTS

| | | | | |
|---|---|---|---|---|
| 1,069,874 A | * | 8/1913 | Hansoom | 132/329 |
| 1,637,153 A | * | 7/1927 | Lawton | 401/34 |
| 2,981,264 A | * | 4/1961 | De Felice | 132/323 |
| 3,078,856 A | * | 2/1963 | Bender et al. | 132/321 |
| 3,939,520 A | * | 2/1976 | Axelsson | 15/167.1 |
| 4,034,770 A | * | 7/1977 | Trecker | 132/321 |
| 4,142,538 A | * | 3/1979 | Thornton | 132/321 |
| 4,550,741 A | * | 11/1985 | Krag | 132/321 |
| 4,729,392 A | * | 3/1988 | Tenny | 132/323 |
| 4,836,226 A | * | 6/1989 | Wolak | 132/321 |
| 4,974,614 A | * | 12/1990 | Selker | 132/321 |
| 4,974,615 A | * | 12/1990 | Doundoulakis | 132/321 |
| 5,035,252 A | * | 7/1991 | Mondre | 132/321 |
| 5,038,805 A | * | 8/1991 | Lee | 132/321 |
| 5,063,948 A | * | 11/1991 | Lloyd | 132/321 |
| 5,316,028 A | * | 5/1994 | Flemming | 132/329 |
| 5,433,226 A | * | 7/1995 | Burch | 132/321 |
| 5,549,201 A | * | 8/1996 | Braude | 206/388 |
| 5,769,225 A | * | 6/1998 | Braude | 206/388 |
| 5,799,673 A | * | 9/1998 | Amendola et al. | 132/321 |
| 5,881,745 A | * | 3/1999 | Landis | 132/323 |
| 5,947,132 A | * | 9/1999 | Swanson | 132/321 |
| 5,970,992 A | * | 10/1999 | Anderson | 132/323 |
| 6,003,525 A | * | 12/1999 | Katz | 132/321 |

(Continued)

*Primary Examiner* — Vanitha Elgart
(74) *Attorney, Agent, or Firm* — Mark M. Friedman

(57) ABSTRACT

Provided is a flossing device comprising a dental floss in the shape of two round members and one straight member in a junction area between them, the device not only entering between the teeth, but cleaning the whole teeth-surface surrounding the inter proximal space. The floss of the device may be impregnated with cosmetic or medical agents.

10 Claims, 14 Drawing Sheets

(56) References Cited

U.S. PATENT DOCUMENTS

| | | | | |
|---|---|---|---|---|
| 6,112,753 A * | 9/2000 | Arsenault | | 132/323 |
| 6,220,257 B1 * | 4/2001 | Meyer et al. | | 132/323 |
| 6,250,313 B1 * | 6/2001 | Rees | | 132/321 |
| 6,340,027 B1 * | 1/2002 | Hagne et al. | | 132/321 |
| 7,156,109 B2 * | 1/2007 | Sampson | | 132/323 |
| 8,069,865 B1 * | 12/2011 | Winter | | 132/323 |
| 2003/0154998 A1 * | 8/2003 | Falleiros et al. | | 132/321 |
| 2005/0016563 A1 * | 1/2005 | Prins | | 132/321 |
| 2005/0061354 A1 * | 3/2005 | Dill, III | | 132/321 |
| 2005/0087208 A1 * | 4/2005 | Satary-Ravabakhsh | | 132/321 |
| 2005/0279378 A1 * | 12/2005 | Lorch | | 132/321 |
| 2006/0005855 A1 * | 1/2006 | Tse | | 132/323 |
| 2006/0201530 A1 * | 9/2006 | Monroe | | 132/321 |
| 2006/0207628 A1 * | 9/2006 | Millis | | 132/321 |
| 2006/0225764 A1 * | 10/2006 | Mark | | 132/321 |
| 2006/0243298 A1 * | 11/2006 | Hamant | | 132/321 |
| 2008/0113315 A1 * | 5/2008 | Beggs | | 433/149 |
| 2008/0163888 A1 * | 7/2008 | Chen | | 132/323 |
| 2008/0314406 A1 * | 12/2008 | Barrie | | 132/329 |
| 2009/0020134 A1 * | 1/2009 | Tomsic et al. | | 132/327 |
| 2010/0116287 A1 * | 5/2010 | Cohen | | 132/323 |
| 2013/0061864 A1 * | 3/2013 | Orma | | 132/200 |

* cited by examiner

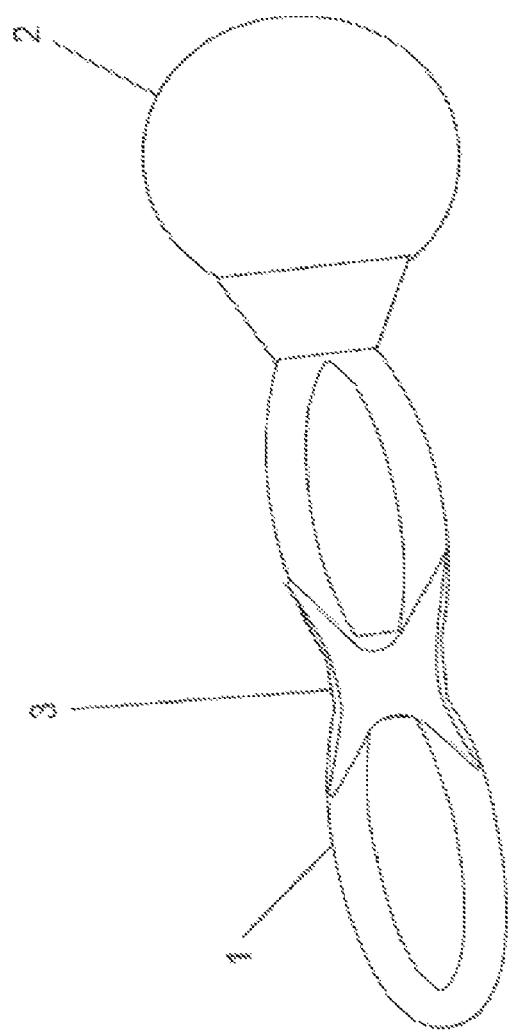

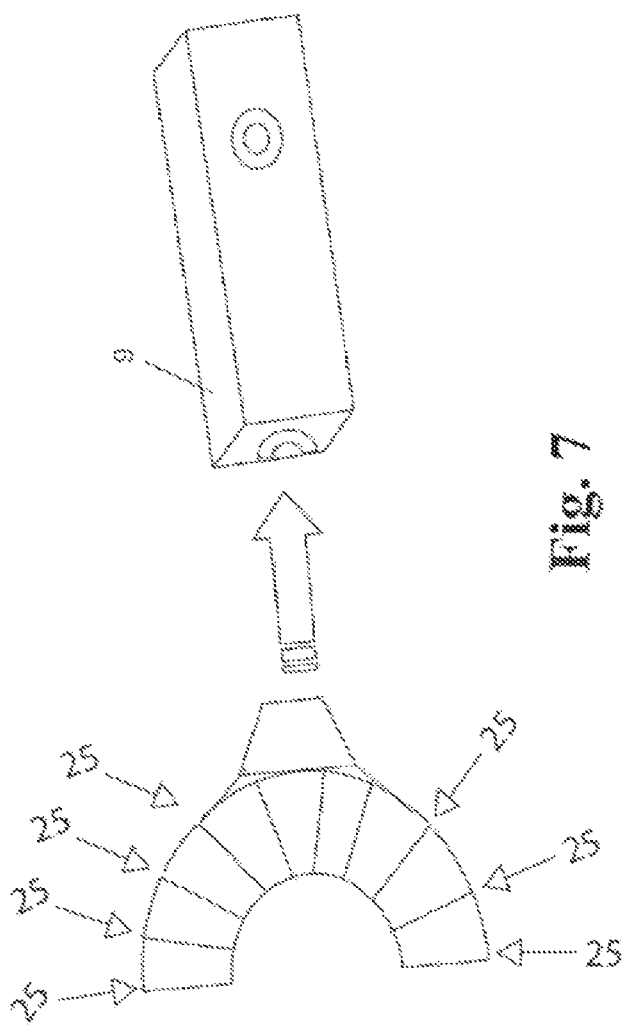

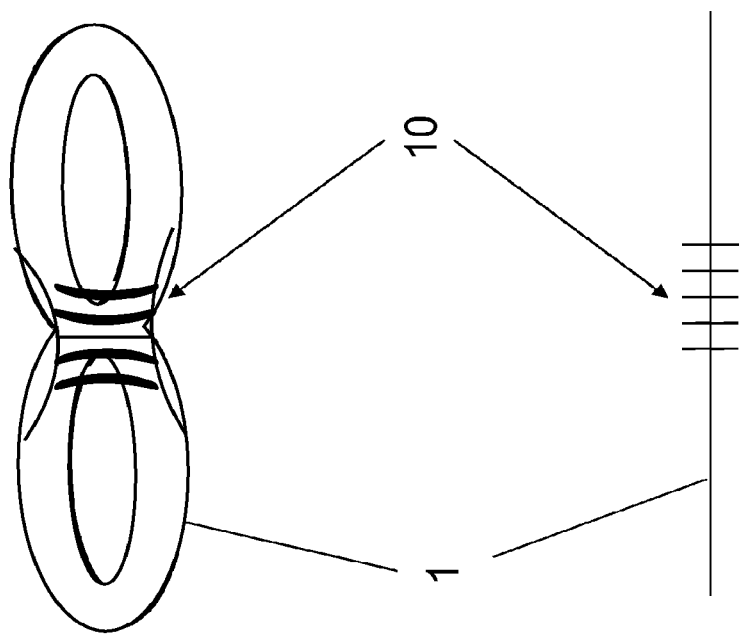

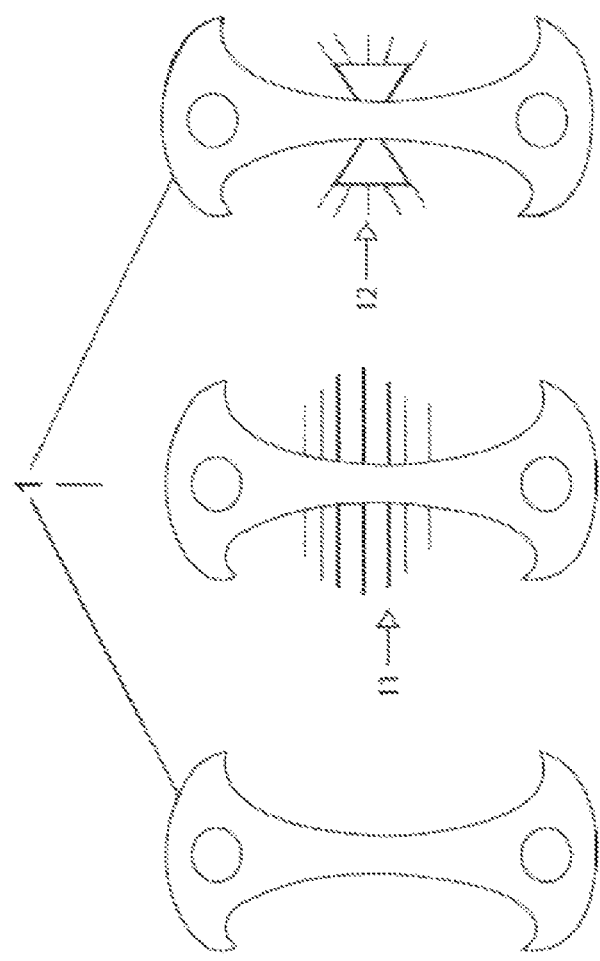

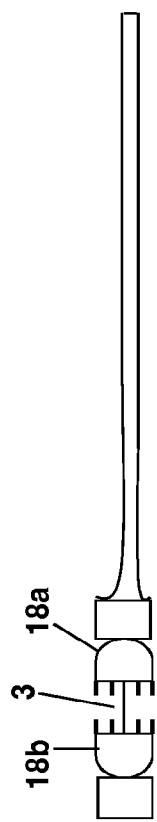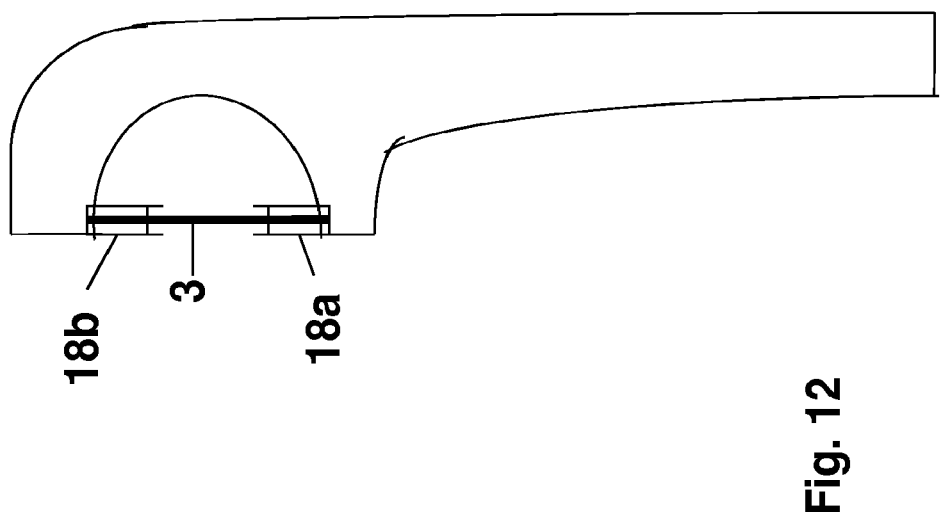
Fig. 12

FLOSSING DEVICE

FIELD OF THE INVENTION

The present invention relates to a flossing device consisting of three members, two lateral and one medial, the medial member cleaning the inter-proximal space, and the lateral members cleaning the front and back parts of the teeth surrounding the space, as the device is pulled and pushed through said space.

BACKGROUND OF THE INVENTION

Dental floss has been found to be useful in controlling gum diseases, reducing bad breath, and helping in plaque removal. Therefore, it is logical that more and more people look for a method for using floss which has a more effective flossing action and is more comfortable to use.

Over time many different approaches and techniques have been used in the development of floss devices. The prior art relates to the development of many devices, ranging from simple spool-like products to complex floss applicators comprising storage chambers.

Two types of inter-dental cleaning devices exist: the first are hard devices, such as tooth-picks; and the second are dental filament devices, such as dental floss and products comprising it.

The use of floss holders consisting basically of common structural designs with (mainly) a single linear floss, is well known in the art.

U.S. Pat. No. 5,947,132 discloses an individual flossing loop, and a cascade of said loops, which may be easily detached from one another. U.S. Pat. No. 3,942,539 relates to a dental floss comprised of a first portion of conventional dental floss, and a thicker second portion having means for retaining antiseptics. U.S. Pat. No. 5,022,417 relates to a flossing mouthpiece for simultaneously flossing a plurality of spaces between adjacent teeth. US 2001/0029962 relates to a dental floss that has a high strength inner core and an outer layer or wrapped sheath. U.S. Pat. No. 6,340,027 relates to an extensible monofilament dental floss, which undergoes a permanent deformation prior to use. US 2003/0230319 relates to a flavor-enhanced dental floss that provides a long lasting release of flavor and/or additional chemicals for providing supplementary therapeutic or cosmetic effects.

Only few publications relate to further unique possibilities. Among them, U.S. Pat. No. 5,970,992 relates to a dental flossing device comprising an elongated arched bow with two integrated floss loops stretched between the arch hands. GB 2349338 relates to an inter-dental cleaning filament comprising one or more closed floss loops. U.S. Pat. No. 4,332,559 relates to a U-shaped dental floss device having a plurality of parallel flosses.

All of the known flossing devices of the prior art are disadvantageous in that they need to be maneuvered, thus making them uncomfortable to use, they are time consuming and they have limited effectiveness/surface contact.

It is, thus, an object of the present invention to provide a new dental flossing device which has the advantages of the well-known existing flossing devices together with additional novel features, resulting in a device with superior flossing action. The device of the invention fills the inter-proximal space most efficiently hence the efficiency of the floss is improved, while minimizing the users handling. The novel features of the device include, but are not limited to, relatively easy development, easy & cheap manufacturing, distinctively improving the teeth surface area contact and is ergonomically advantageous.

It is an important object of the invention to clean both the inter-proximal space and the surface of both teeth surrounding the space.

It is another object of this invention to provide a novel dental flossing device, comprising a floss portion in the shape of the numeral eight and a gripping or maneuvering extension portion, for removing food and debris from between teeth and crowns, and for delivering medical and/or cosmetic agents to the inter-proximal spaces.

In yet another object of this invention, the flossing portion rotates, via a connector that connects it to the gripping or maneuvering extension potion, as it works in the inter-proximal space between adjacent teeth.

It is another object of this invention to provide a method for producing said flossing device.

Other objects and advantages of present invention will appear as description proceeds.

SUMMARY OF THE INVENTION

The invention provides a flossing device for cleaning an inter-proximal space and the surface of the teeth surrounding said inter-proximal space, comprising three members, two lateral and one medial, in a fixed position toward each other, said lateral members being elastic and essentially wider than said inter-proximal space, and said medial third member placed in the area between said two lateral members, the first lateral member is spaced from the second lateral member so that (i) a portion of the first member cleans front parts of the teeth surrounding said inter-proximal space, and a portion of the second member cleans back parts of the teeth surrounding said inter-proximal space, when said third member moves back and forth, and up and down, through the inter-proximal space while cleaning it, and (ii) said lateral members collapse onto the teeth's surface, when said medial member is pushed or pulled through said inter-proximal spaces, and essentially abut against the whole teeth-surface surrounding said inter-proximal spaces, returning to their shape after the use. Said members may comprise any dentally acceptable material, including polymers, nontoxic metals, or ceramics. In a preferred embodiment, said material comprises polymers. Said lateral members may have any shape suitable for effective cleaning the tooth surface and the interproximal spaces, while removing any foreign residues without wounding the teeth or the tissues of the user; they may, for example, have essentially the shape of loop, semicircle, sphere, or hemisphere. Said third member lies in the junction area between said round members. In one embodiment of the invention, said third member connects said two round members. In a preferred embodiment, said third member is essentially straight. Said straight member may be a dental floss. In one embodiment, said members comprise dental floss or wire. Any floss, floss-like material, or wire-like material, suitable for cleaning the teeth surface and the inter-proximal spaces may be comprised in the device of the invention, including available commercial materials. In a preferred device of the invention, said members comprise on their surface structures improving the cleaning action, for example indentations, projections, hairs, and roughening structures, which. In one embodiment, the medial member comprises on its surface hair or roughening structures; in another embodiment, all the members comprise said hair or roughening structures. Said roughening structures may comprise indentations on the surface of the device members; said roughening structures may comprise projections on the surface of the device members.

On one aspect, the invention provides a flossing device as described above for cleaning an inter-proximal space and the teeth surface surrounding said inter-proximal space, comprising: (A) an elastic dental floss having a first loop in a fixed position toward a second loop, and a junction area between the loops wherein (i) the junction area can withstand forces, without normally breaking, when pushed or pulled through said inter-proximal space and (ii) the first loop is spaced from the second loop so that (a) a portion of the first loop cleans front parts of the teeth surrounding said inter-proximal space and (b) a portion of the second loop cleans back parts of the teeth surrounding said inter-proximal space when the junction area moves back and forth through the inter-proximal space, and further having (B) a gripping portion attached to at least one of said loops, said floss returning to its shape after being pushed or pulled through said inter-proximal space. In one embodiment, one of said lateral members in the device of the invention is attached to said gripping portion. In another embodiment, all three members in the device of the invention are attached to said gripping portion. In one preferred embodiment of the invention, the lateral members of the flossing device have the shape of two identical loops. In a device according to the invention, the floss that is employed may be impregnated with a substance selected from the group consisting of a strong flavor substance, an antiseptic, a gingivitis affecting agent, a supporting agent for quitting smoking, a fluoride, a breath freshener, a pH modifier, a tooth whitener, and another therapeutic substance. In another aspect of the invention, provided is a flossing device, comprising (i) a plurality of dental floss portions; (ii) a dental comb, in which the floss portions are mounted upon; (iii) a grip; and optionally (iv) a means for delivering a flavor and/or a therapeutic substance to the oral cavity, the means comprising floss impregnation; wherein said dental floss portions are in the shape of the numeral eight. The therapeutic substance used in a device according to the invention may include at least one of nicotine based therapeutic drug, a fluoride-based tooth enamel hardener, a breath freshener, a base for neutralizing stomach acid, a stomach acid inhibitor, anti-gingivitis medicament, and a tooth enamel whitener. The device according to the invention may comprise a polymer selected from acrylics, polyolefins, polyesters, polyamides, polycarbonates, halogenated polyolefins, and mixtures thereof. Said polymer may comprise an injection molded plastic. In a preferred embodiment of the device according to the invention, the floss portion or the gripping portion, or both, are coated with a reinforcement material. Said reinforcement material may comprise, for example, polyamide.

In one aspect of the invention, provided is a device for cleaning an inter-proximal space and the surface of the teeth surrounding said inter-proximal space, comprising three polymeric members, two lateral and one medial, wherein said two lateral members are loops which provide the shape of the numeral eight, the loops touching each other at a junction area, wherein said junction area may be reinforced. Said junction area is preferably reinforced, for example with a wire; said junction area may be coated with a membrane. The floss may be coated with microcrystalline wax.

The flossing device of the invention preferably comprises elastic dental floss and/or exhibits flexibility and collapses onto the teeth's surface, when being pushed or pulled through said inter-proximal spaces, and essentially abuts against the whole teeth-surface surrounding said inter-proximal spaces.

The invention is directed to a method of manufacturing the flossing device of claim 1, comprising (i) forming a floss portion in the shape of two loops and a junction area between them; (ii) reinforcing said junction area and/or coating it; and (iii) attaching one of said loops to a polymer gripping portion. In one embodiment, the method of the invention further comprises a step of impregnating said floss with a material selected from flavor substances and medical agents. In one embodiments of the method, the floss portion and/or the gripping portion are coated with a reinforcement material. In other preferred embodiment, the junction area in the floss portion is reinforced with a wire. The junction area in the floss portion may be coated with a membrane. Said device may comprise a plurality of flossing portions mounted onto a dental comb. Said medical agent in the method of the invention may be selected from antiseptic, pH modifier, and an agent affecting gingivitis. In a preferred embodiment, said material comprises menthol or a peroxide.

Said floss-impregnating substance, selected from flavor substances, antiseptics, gingivitis affecting agents, supporting agents for quitting smoking, fluorides, breath fresheners, pH modifiers, tooth whiteners, or other therapeutic substances, are preferably released from the floss during the flossing action. Said floss portion may be made of a polymer selected from acrylics, polyolefins, polyesters, polyamides, polycarbonates, halogenated polyolefins, cellulose and mixtures thereof; non-limitative examples may comprise polymethyl methacrylate, polyethylene, polypropylene, polycaprolactone, nylon, polycarbonate, PTFE, etc. Said floss portion may be coated with microcrystalline wax, into which active components may be incorporated, such as anti-caries, anti-plaque, antibacterial, or various dentally acceptable agents such as polishing and abrasive agents, etc. Known methods may be employed when manufacturing the floss portion of the device, and the gripping portion. The floss portion may be manufactured by including any process that manipulates a single/multiple thread/s to a suitable shape, such as comprising two loops, and then thermally fixing it, or a method that stamps out the shape, like the shape of figure eight, and then further treating or using the appropriate glue to create the desired figure. Said device may optionally be formed from an injection molded plastic. The floss portion and/or the grip portion may be coated with a reinforcement material. In a preferred embodiment said reinforcing material comprises polyamides, like Kevlar® or others. The junction area in a shape comprising said three members, for example the junction area between two loops, for example the area at which two loops meet, may comprise glue bonding two threads, and/or reinforcing the area, for example with a wire portion. Said junction area may be coated with a layer, such as a plastic layer or a membrane.

The junction area of the device of the invention has multiple functions: i) to penetrate the interproximal space of two adjacent teeth; and ii) to abut against the contour of teeth surface area so as to address any contour created by different interproximal spaces of different teeth (adjacent front teeth will create a different contour surface area than adjacent molers). This is effect is enhanced by different add-ons to the junction area that do not impede the penetration of the interproximal space and which abut against different surface area contours (see e.g. FIGS. 2-4, 8 and 10). Additionally, the scraping/friction action due to the double axe shape of the device of the invention against the front or back of the teeth, enables flossing of the inter proximal space and beyond.

For each embodiment of the flossing device of the invention there may be a preferred production method and material/s used; e.g. when producing the flossing device as described in FIG. 9, the production method and materials used should be chosen from those that will provide the device with high spring like characteristics.

In one special embodiment, the invention relates to a method of forming the flossing device which has a floss in the shape of the numeral "8" or the symbol for infinity, comprising i) forming a floss portion in the shape of the numeral eight, the shape of said numeral comprising two loops touching each other at a junction area, wherein said two loops in fact form one physical body; ii) reinforcing said junction area and-or coating it; and iii) attaching one of said loops to a polymer gripping portion, the attachment being located at a distal part of the loop relatively to said junction. The method of the invention preferably comprises forming a means for delivering various substances to the oral cavity. The method may further comprise the steps of coating and/or reinforcing the floss. The junction area in the floss portion is preferably reinforced, sufficiently to penetrate the inter proximal spaces, possibly with an embedded wire or other consistency or by coating it with various strengthening means, hence enhancing rigidity as well as the ability to withstand the forces upon it as it works in and around the inter-proximal area. The junction area in the floss portion of the device may be coated with a membrane or sandwiched between two layers of a membrane (which will become one). In one aspect, the invention provides a method for forming a flossing device comprising a plurality of the flossing portions, which are mounted onto a dental comb. The floss of the device of the invention is in a preferred embodiment impregnated with a material selected from flavor, antiseptic, pH modifier, and an agent affecting gingivitis. Said impregnating material may comprise menthol; it may comprise a peroxide, preferably a solid peroxide.

The present invention thus provides a three-member flossing device, for example in the shape of the two round members and one medial member between them, wherein said round members have dimensions greater than typical inter-proximal spaces. The device of the invention is preferably formed of a polymeric material, and most preferably is coated with a reinforcement material or manipulated in a chemical and/or heat curing procedure while keeping its ability to elongate/contract while remaining relatively rigid, returning to it's original shape. For further strengthening the rigidity, a wire or membrane may be embedded in or surround the junction area. Specially, the invention relates to a flossing apparatus comprising a dental floss in the shape of the numeral eight, and to a method for forming such an apparatus, wherein said method includes steps of creating a figure "8" from a flossing ribbon, and connecting said figure with a gripping means.

BRIEF DESCRIPTION OF THE DRAWINGS

The above and other characteristics and advantages of the invention will be more readily apparent through the following examples, and with reference to the appended drawings, wherein:

FIG. 4. is a scheme illustrating an alternative addition to the flossing device of the invention, comprising a membrane around the junction area;

FIG. 7. is a scheme illustrating an embodiment of the invention, comprising a plurality of flossing devices mounted to form a dental comb;

FIG. 8. illustrates another embodiment of the flossing devise of the invention, in which said device additionally comprises flexible ribs that enable brushing of the gums area, FIG. 8a being a top view and FIG. 8b side view;

FIG. 10. illustrates another embodiment of the flossing devise of the invention, in which said device is without (FIG. 10a) or with additions (FIG. 10b and FIG. 10c) that enable brushing of the gums area and/or clean out any contour it encounters;

FIG. 12. shows a device according to another embodiment of the invention, comprising three members mounted on the grip portion; lateral members 18a, 18b have hair-like projections emanating towards central flossing element 3. Lateral members 18a, 18b collapse onto the teeth and clean their surfaces;

FIG. 14A shows said device moving between the teeth and cleaning the inter-proximal space by supplementary bristle elements 3 sticking from the medial member; FIG. 14B shows member 20a touching the back parts of the teeth surrounding said inter-proximal space, and acting to remove residues 5; FIG. 14C shows the device being pulled so that the flexible loop 20*a* is deformed and abuts onto the back parts of the teeth surrounding said inter-proximal space and covers a still greater part of the teeth surface, optimally the whole of it, reaching the residues 5 and removing said residue; FIG. 14D shows the device being pushed back while the loop 20*a* acquires its original shape and the loop 20*b* approaches the front part of the teeth surrounding said inter-proximal space; FIG. 14E shows loop 20*b* being deformed and collapsing onto the teeth, as the device is pushed still further between the teeth, and reaching an impurity 6 on the front part of the teeth; FIG. 14F shows the device pulled back, while both back and front parts of the teeth are cleaned of the residues 5 and 6, while lateral loops 20*a* and 20*b*, in a fixed position toward each other and essentially wider than said inter-proximal space, return to their shape after being pushed and pulled repeatedly through said inter-proximal spaces.

DETAILED DESCRIPTION OF THE INVENTION

In view of the numerous flossing devices of the prior art, the present invention provides for a novel device for flossing teeth, wherein the floss portion in said device is shaped like the numeral eight.

Figure 1:
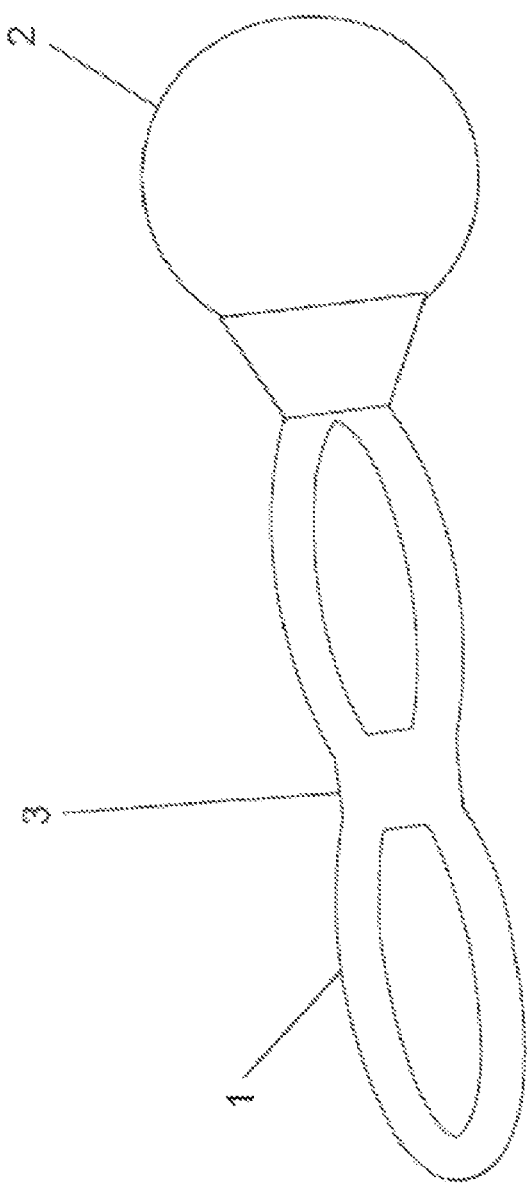
FIG. 1. is a scheme illustrating the flossing device according to one embodiment of the invention.

The invention consists of a flossing device comprising a floss portion (1) in the shape of the numeral eight or the sign for infinity and a gripping portion (2), as shown in FIG. 1. Said gripping portion might be jointed to enhance the user's ability to reach easily inter proximal spaces. The device preferably is made from a polymer, or other suitable material, and preferably is coated with a reinforcing material, such as Kevlar® fibers (Poly-paraphenylene terephthalamide hereafter), for added strength, without compromising its elasticity and its ability to return to its original shape. Further to strengthen the rigidity of the device, a wire or wafer of sufficient capabilities may be embedded throughout the framework, or specifically in the junction area (3). For penetrating the inter-proximal space, one must align the junction area to the inter-proximal space, then force the junction area to overcome the initial resistance of the teeth, while forcing the junction area to contract and stretch (due to the applied forces and the friction of the teeth surfaces). The device then tries to return to its original width and shape that is enabled by the space-abutting.

The width of the junction area in one preferred embodiment of the device is approximately 50-200 microns, which is intended to be able to penetrate the inter-proximal space between adjacent teeth.

The dental floss device of the present invention may be made of any suitable material known in the art. Suitable materials include polymers such as, but not limited to, acrylics, such as poly methyl methacrylate; polyolefins, such as polyethylene and polypropylene; polyesters or polyamides, such as comprising caproic acid; co-polyesters; polycarbonate, PTFE; and mixtures thereof.

The dental floss device of the invention may comprise expanded polytetrafluoroethylene having a high tensile strength; it may comprise other suitable polymeric matrix with a high strength known in the field; a coefficient of friction of the floss may be modified to increase the efficiency of the cleaning activity, for example, by adhering a microcrystalline wax to the surface of said polymer.

The grip portion and the floss portion of the device of the present invention may be made of the same material or different materials. Preferably, the floss portion is made of a material that is softer than the material from which the grip portion is made. The device of the present invention may be made by any suitable process known in the art, e.g. injection molding, or by coating fibers, using molds of required geometry.

The floss portion in the device of the present invention may be woven, ribbed, fluffy or otherwise multi-fiber, or may be impregnated with wax, or otherwise treated. The device may also comprise PTFE. The floss portion of the present device may be additionally coated e.g. with flavor additives and/or any pharmaceutical compound. the floss may be prepared from a material which is suitable for administrating various compositions to the mouth of the user, and/or to the interdental area, and/or the gum area in between two adjacent teeth.

In one of its aspects this invention relates to an improved combination of a dental floss device with the addition of a medicament. In another one of its aspects, this invention provides a device assisting tooth cleaning, and orally administrating a medicament, wherein said medicament may be a fluoride, a nicotine-based drug, a breath freshener, a base, a stomach acid inhibitor, an enamel whitener, a combination of the foregoing or any other therapeutic substance. The device combines use of a dental floss with oral administration of medical or cosmetic agents.

In a preferred embodiment, the device of the invention comprises a mint-type, flavored medicament, which will freshen the breath; an antacid medicament, which will reduce acid reflux as experienced by many; or a fluoride medicament, which will help prevent cavities.

Another aspect of this invention provides a package containing the dental floss-based tooth cleaning device and an agent for oral administration, medical or cosmetic.

In another aspect of this invention, provided is an improved dental floss device, which includes multicomponent co-extruded filaments and/or filaments having a multilobal cross-section. Optionally, the floss of the invention is capable of bulking.

Figure 2:
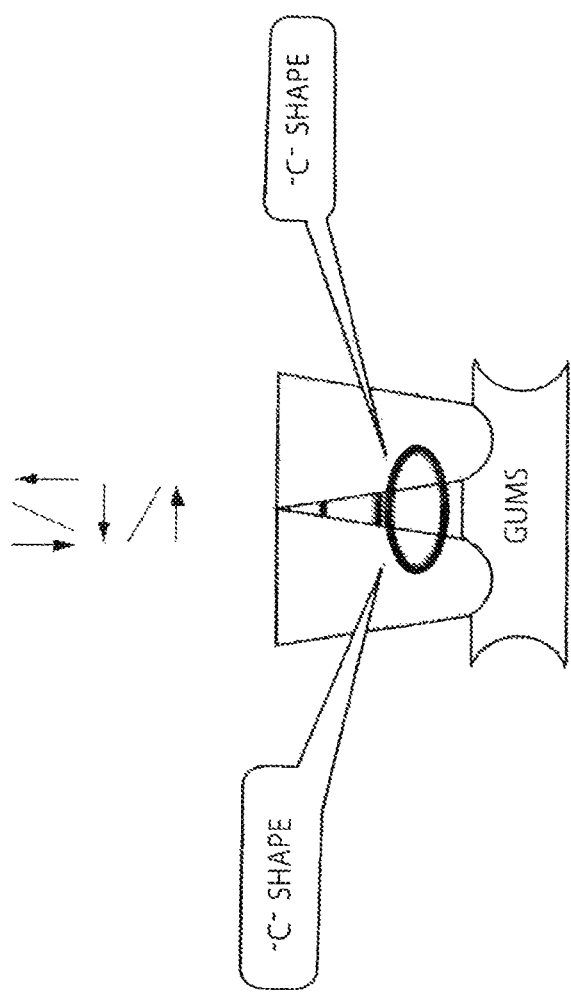
FIG. 2. is a scheme illustrating the flossing device of the invention penetrating the interproximal space and maneuvered up/down, left/right and forward/backward, and the created "C" shape contact a portion of the front and back teeth.
Figure 3A:
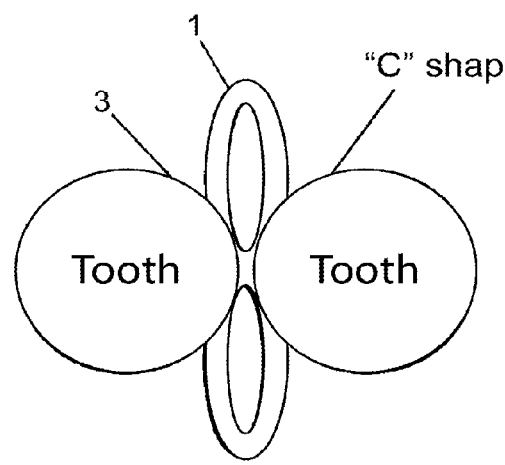
FIG. 3. is a scheme illustrating an operation possibility of the flossing device of the invention, FIG. 3a showing tight adjoining of the device to the teeth-surface surrounding the inter proximal space, creating a "C" shape contact curvature, FIG. 3b illustrating the device flexibility during pulling it through the inter proximal space, FIG. 3c showing the return to the original form of the device when being pushed back, and FIG. 3d showing maintaining the device flexibility when pushing it still farther to the opposite direction.
Figure 3B:
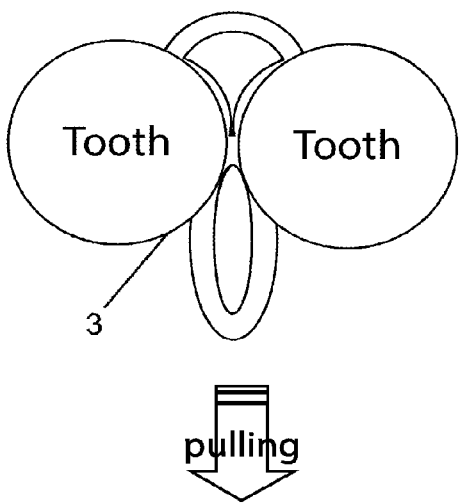
Figure 3C:
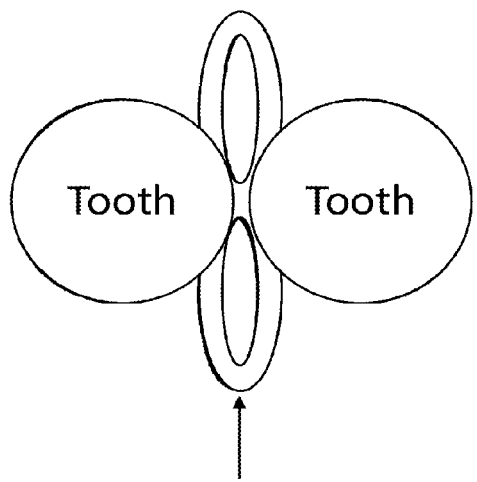
Figure 3D:
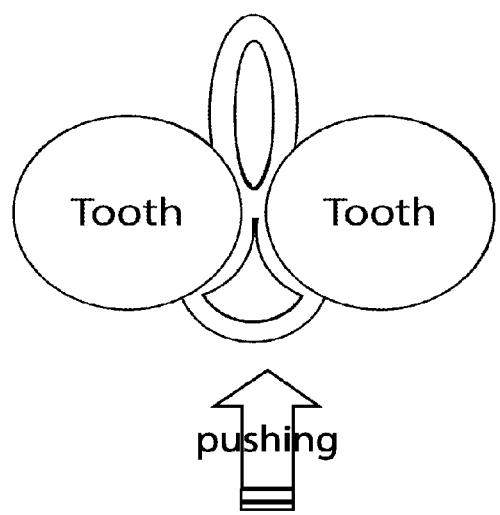

As a result of the unique geometric shape of the device, it is possible to perform flossing of the inter-proximal space, for example, using one hand, in an inward/outward and/or up/down movement of the device. As illustrated in FIG. 2, the user must first penetrate the inter-proximal space using the middle of the numeral eight—the junction area (3). Afterwards, the device is moved up/down, left/right and forward/backward to achieve cleaning of the inter-proximal space. When the device of the invention is used, the figure eight flossing portion collapses and the resistance creates friction at a portion of the back and front of adjacent teeth—and not only between the teeth. In order to achieve best flossing results, the thickness of the floss used is chosen according to the inter-proximal spaces of the user, so that maximum contact is maintained between the teeth and the device (i.e. for wide spaces one would use thicker floss and vise versa). As illustrated in FIG. 3, after inserting the device, in between the inter proximal space of two adjacent teeth, the device is under pressure from both sides by the teeth and has been squeezed sufficiently without loosing it's rigidity and basic form (FIG. 3*a*). When the device is pulled towards one way, the opposite end collapses on to the teeth's surface area while creating friction (FIG. 3*b*). In the meanwhile the junction area (3) of the device is creating friction hence cleaning in the inter proximal space. as a result of pushing the device back, it retains its basic shape (FIG. 3*c*) and is ready for the next step of the flossing action; now the device is pushed towards the opposite direction, making the pushed upon end collapse on to the teeth's surface area while creating friction (FIG. 3*d*). In the meanwhile the junction area (3) of the device is creating friction hence cleaning in the inter proximal space. Furthermore, the flossing action, utilizing the unique geometric shape of the device, creates a "C" shaped tangent to the surface area of the adjacent teeth, so as to cover the area to be cleaned. In contrast to various conventional dental flosses, the device of the invention not only enters the inter proximal space, but essentially abuts against the whole teeth-surface surrounding said inter-proximal space. The required rigidity of the device can be attained, even at the preferred thickness of 50-200 microns, by using known polymeric materials, eventually combined with reinforcing fibers, either fragmented or continuous. For example, reinforcement with Kevlar® fibers may provide the preferred flexibility and strength (e.g., elasticity module of 100 GPa, tensile strength of 3 GPa).

Furthermore, when addressing uneven spaces (e.g. crooked teeth) the device of the invention has a distinctive advantage where the loops of the numeral eight fill the inter-proximal spaces as the device is pulled or pushed, while creating friction and thus flossing. When using the device of the invention, while pulling and pushing it, the figure eight collapses and then returns to the original shape; the loops are not pulled through easily, the resistance creating friction at a portion of the back and front of adjacent teeth—and not only between the teeth. Notably, even when the teeth structure is such that the inter proximal space grows at the base (e.g. in crooked teeth) the figure eight shaped device of the invention fills the space, thus creating effective continuous flossing action.

In one aspect, the device of the present invention can be augmented with a membrane at the junction area for added teeth-surface friction and rigidity, without compromising its ability to penetrate the inter proximal space. An example of a device according to the invention is presented schematically in FIG. 4 to which the following description refers. The membrane (5) adds not only rigidity to the whole structure, especially the junction area (3), but a means to "hug" the surface areas of the teeth, and optionally delivering medicine. Preferably, an indication to replace and use a new device will be provided as the membrane falters. Preferably, the membrane profile will not be more than about 50-200 microns in thickness. The profile cross-section illustrated is the preferred profile design, at present, for enhancing rigidity and functionality.

An array of different holding surfaces may be attached to the device such as a pad, an elongated plastic cone, or a jointed, elbow type, with which it is easier to pivot and manipulate the device, etc.

Figure 5A:
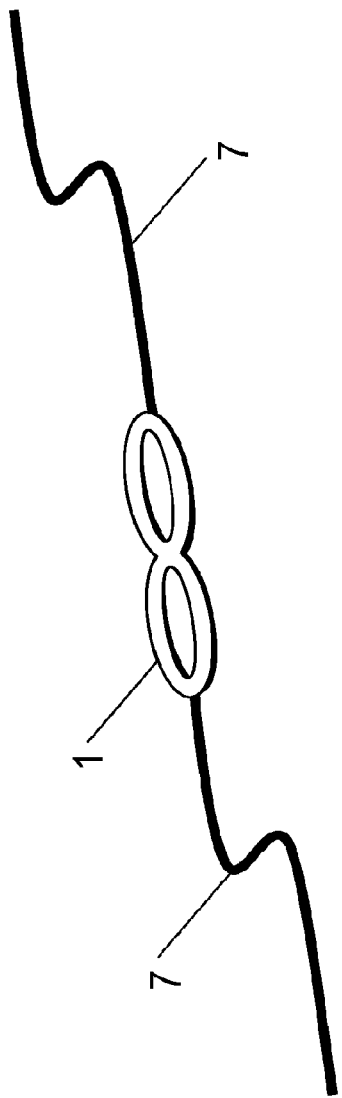
FIG. 5. is a scheme illustrating another embodiment of the flossing device of the invention, FIG. 5a showing a pulling string attached at the two points of the flossing portion, FIG. 5b showing a "flossing ring"
Figure 5B:
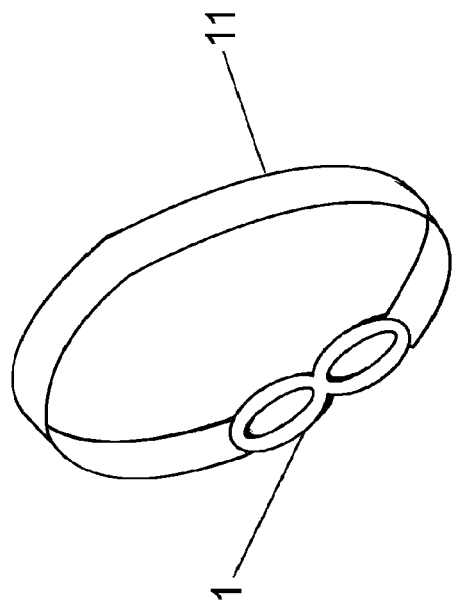

According to anther embodiment of the invention, and as illustrated schematically in FIG. 5a, a thin rope/string (7) can be connected to the flossing portion (1) at each end of the numeral eight. Said points of connection between the strings and loops are reinforced to withstand the pulling forces during use. The user will insert the device in between the inter-proximal space and alternately pull each end of the rope, hence creating flossing action. In a preferred embodiment of the invention, said thin rope may optionally have a loop at each end, so that the user can place two fingers, i.e. a finger at each side of the flossing portion. Alternatively, as illustrated schematically in FIG. 5b, a ring (11) can be connected to the flossing portion (1) at each end of the numeral eight. This "flossing ring" enables the user to handle the flossing device using only one hand.

Figure 6B:
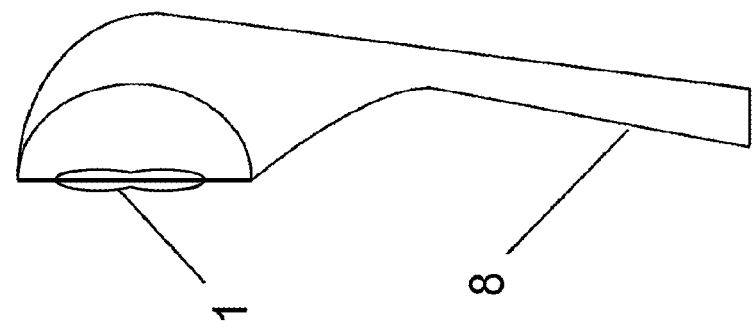
FIG. 6. is a scheme illustrating another embodiment of the flossing device of the invention, comprising an apparatus providing automatic rotation or vibration, FIG. 6a showing mounting the device at one end, FIG. 6b showing mounting the device at both ends.
Figure 6A:
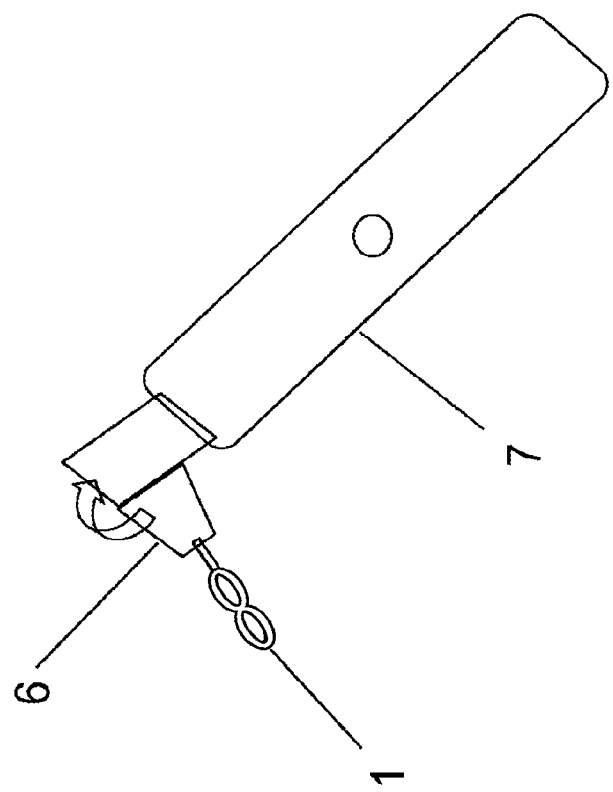

Alternatively, the device could be connected only at one end or between two opposing tongs. The device could than receive vibrating action/or not, as via a hand held electric vibrating machine. One example of such a device is presented schematically in FIG. 6a, where the device (1) can be mounted at one end to the connector (6). Another example of such a device is presented schematically in FIG. 6b, where the device (1) can be mounted at both ends, directly to the connector (6) or in between two plastic tongs also termed "a gripping handle" (8). Said connector may be capable of rotating. Said connector, in turn, is fastened to a vibrating machine (7), preferably an electric or electronic vibrating device, which vibrates and/or rotates (via the connector) the device as it works in the inter-proximal space between adjacent teeth.

According to yet another embodiment of the invention, two or more of such devices could be mounted as part of a dental comb. As illustrated in FIG. 7, a plurality of devices (25) are mounted on a dental comb. Each device is distanced appropriately from its neighbors for substantially simultaneous treatment of all inter-proximal spaces of the teeth in the lower or upper jaw. The dental comb could, optionally, be connected to a vibration transfer machine (9), as shown. In A preferred embodiment, said devices are connected to said comb in a flexible manner in order to achieve better fit of the user's teeth. In yet another preferred embodiment, the distance between said devices could be adjusted and fixed to better fit the user's teeth.

In another aspect, and as illustrated in FIG. 8, flexible ribs (10) are part of the flossing device (1) of the present invention. Said ribs are located at either side of the junction area. Said ribs can enable the brushing action of the gums area in between two adjacent teeth while performing the flossing action.

Figure 9A:
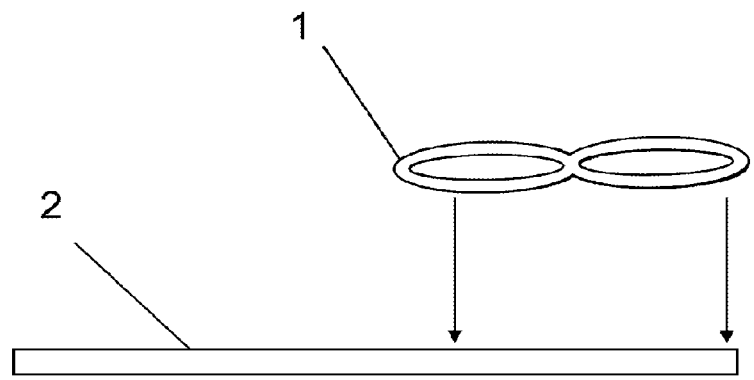
FIG. 9a-c. schematically shows flexibility of the flossing device in one embodiment of the invention, the figure eight is in a spring like arch form pushing outwards.
Figure 9B:
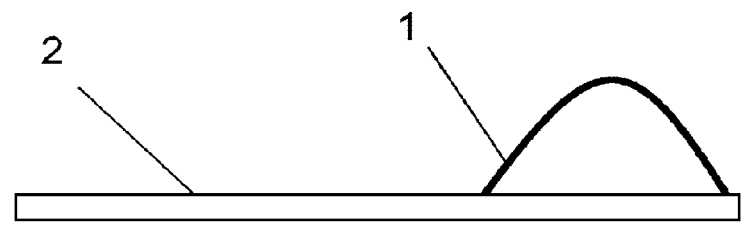
Figure 9C:
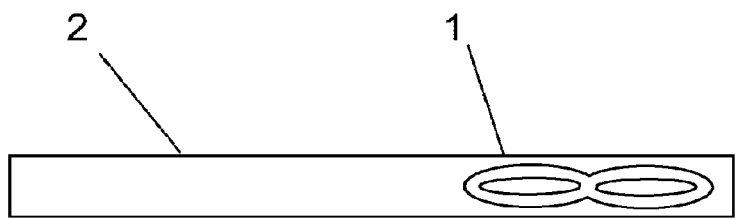
Figure 11:
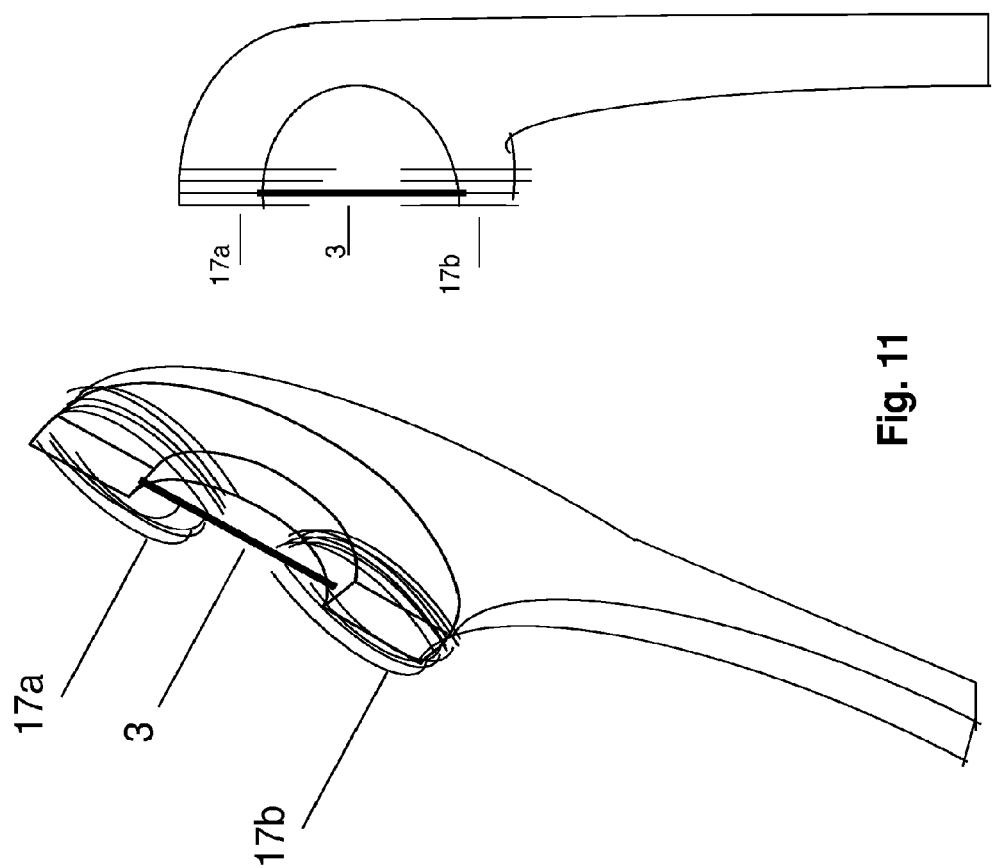
FIG. 11. shows a device according to one embodiment of the invention, comprising three members independently mounted on the grip portion; paired shaped elements 17a and 17b are rounded bristles, and median member 3 is a straight element in the area between the lateral members but stemming from the handle; as the device is being pulled/pushed back and forth, up and down, between the inter-proximal space, the bristles collapse on the surfaces of the back and front teeth causing the cleaning action to occur.
Figure 13:
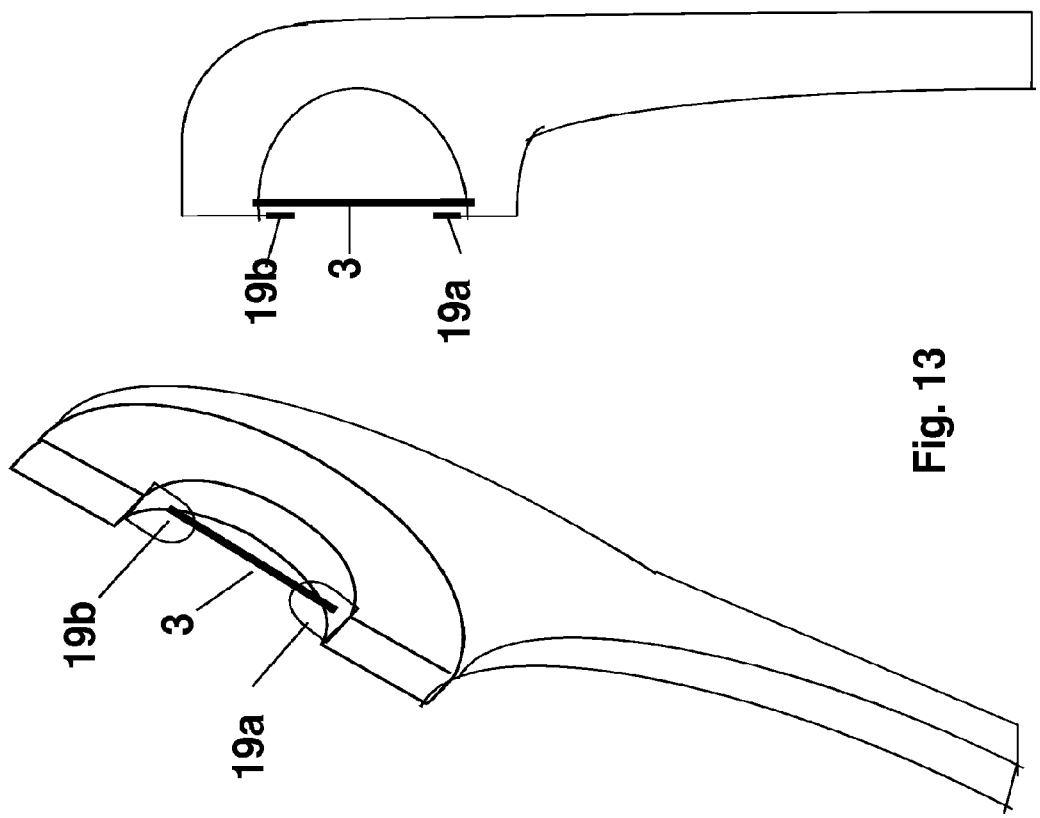
FIG. 13. shows a device according to another embodiment of the invention, comprising three members independently mounted on the grip portion; lateral members 19a, 19b are rounded, and mounted on the grip in one plane. Median flossing member 3 is a straight element mounted on the grip in a parallel plane, best shown in side view (upper figure). The members 19a, 19b and median flossing member 3 having no direct contact. Members 19a, 19b may be positioned either above or below member 3; members 19a, 19b may have a double axed shape being cast above of member 3, which may be a dental floss.
Figure 14:
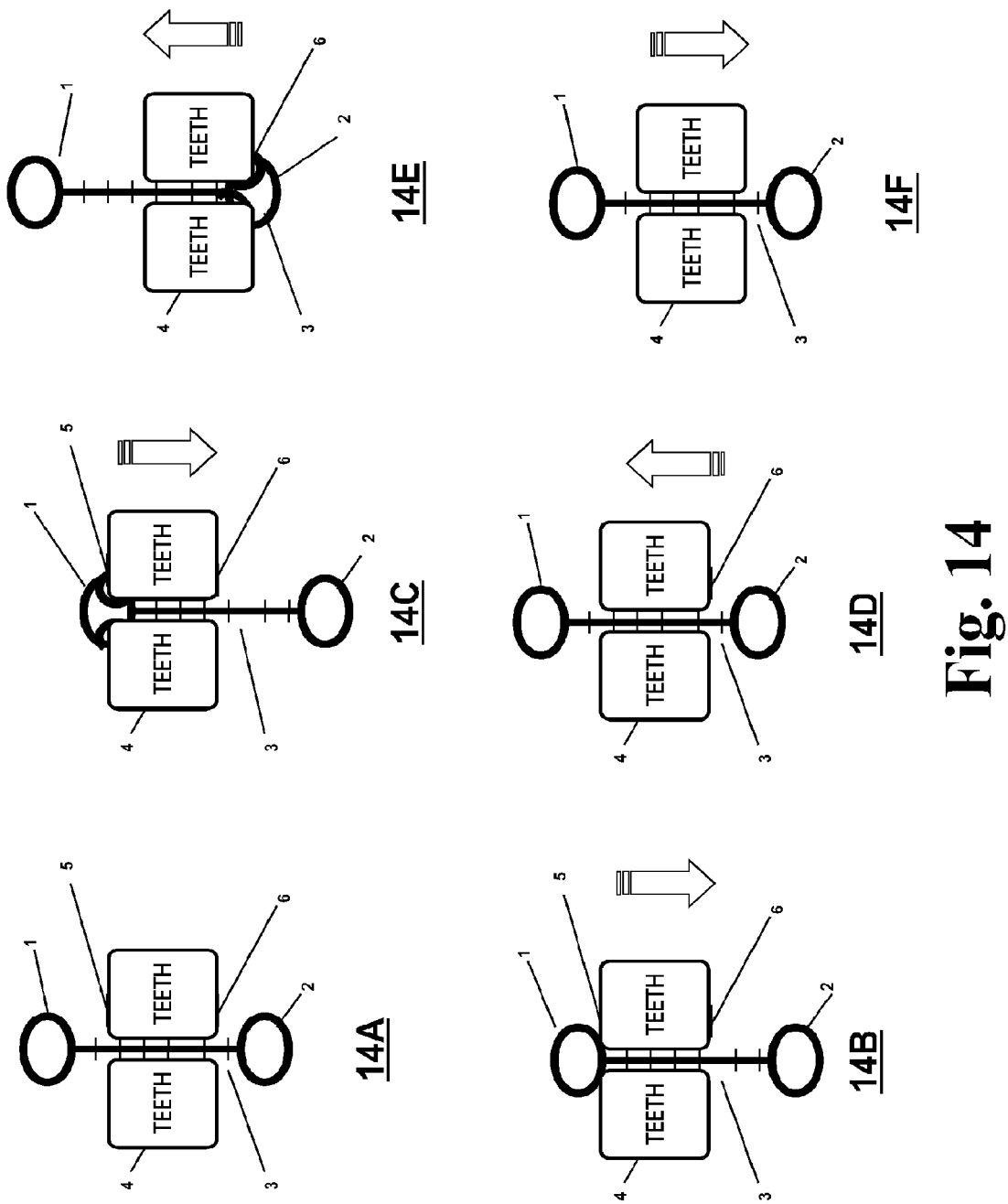
FIG. 14. shows use of the device. In this embodiment, three-member device comprises two lateral members 20a, 20b, and one medial member 3 between said lateral members connecting them. In use, the medial member is inserted into an inter-proximal space between tooth 4 and its neighbor 5.

According to anther embodiment of the invention, and as illustrated schematically in FIG. 9, the figure eight flossing device of the invention (1) may be manipulated and held at a shorter distance than its relaxed length, forcing it to rise, thus creating a flexible arch, with a spring-like action (FIG. 9a—prior to manipulation; 9b—side view; 9c—top view). Once the junction area is inserted in between the inter proximal space, flossing action is administered by the user utilizing the figure eight's special and unique flossing advantages Another aspect of the invention, as illustrated in FIG. 10, the pulling/pushing of the device results in maximal surface contact of said loops with the front and back of the adjacent teeth (FIG. 10a). In addition, FIGS. 10b and 10c, illustrate optional add-ons (10) to the flossing device (1): FIG. 10b illustrates a plurality of supplementary bristles (11) parallel to one another; the supplementary bristles (11) have varied lengths. FIG. 10c illustrates a plurality of bristles (12) angled at a variety of angles, for optimal cleaning. Said add-ons enable both the brushing action of the gums area in between two adjacent teeth, and the clean out of any contour it encounters.

As used herein and throughout, the term "flossing portion" relates to a single floss unit, whereas the terms "loop/s" and "junction area" are used merely to describe the different areas in said flossing portion. Said junction describes the narrow part where the apparent two loops of the figure eight meet.

While this invention has been described in terms of some specific examples, many modifications and variations are possible. It is therefore understood that within the scope of the appended claims, the invention may be realized otherwise than as specifically described.

The invention claimed is:
1. A flossing device for cleaning an inter-proximal space between teeth and the surface of the teeth surrounding said inter-proximal space, comprising:
  (A) an elastic dental floss portion having a first loop in a fixed position toward a second loop, and a junction area between the loops,

(i) the junction area can withstand forces, without normally breaking, when pushed or pulled within said inter-proximal space, and (ii) the first loop is spaced from the second loop so that: (a) a portion of the first loop cleans front parts of the teeth surrounding said inter-proximal space, and (b) a portion of the second loop cleans back parts of the teeth surrounding said inter-proximal space when the junction area moves back and forth within the inter-proximal space, and (B) said floss portion returning to its shape after being pushed or pulled within said inter-proximal space;

said flossing device further comprising:

(i) a plurality of dental floss portions;

(ii) a dental comb, in which the floss portions are mounted upon;

(iii) a lengthened grip having an end into which said dental comb is insertable; and optionally, and (iv) a means for delivering at least one of a flavor or a therapeutic substance to the oral cavity, the means comprising floss impregnation;

wherein each of said dental floss portions is in the shape of the numeral eight.

2. The device of claim 1, wherein said lengthened grip includes a vibrating mechanism for vibrating said device.

3. The device according to claim 1, wherein the therapeutic substance includes at least one of: a nicotine based therapeutic drug, a fluoride-based tooth enamel hardener, a breath freshener, a base for neutralizing stomach acid, a stomach acid inhibitor, anti-gingivitis medicament, and a tooth enamel whitener.

4. A flossing device for cleaning an inter-proximal space between teeth and the surface of the teeth surrounding said inter-proximal space, comprising:

(A) an elastic dental floss having a first loop in a fixed position toward a second loop, and a junction area between the loops, (i) said junction area for withstanding forces, without normally breaking, when pushed or pulled within said inter-proximal space, and (ii) the first loop is spaced from the second loop so that: (a) a portion of the first loop cleans front parts of the teeth surrounding said inter-proximal space, and (b) a portion of the second loop cleans back parts of the teeth surrounding said inter-proximal space when said junction area moves back and forth within the inter-proximal space, and (B) a gripping portion attached to at least one of said loops, said floss returning to its shape after being pushed or pulled within said inter-proximal space; wherein said flossing device is in the shape of the numeral eight, the loops touch each other at said junction area, wherein said junction area is reinforced.

5. The device according to claim 4, wherein said junction area is reinforced with a wire.

6. The device according to claim 4, wherein said junction area is coated with a membrane.

7. A dental apparatus, comprising:

oppositely disposed first and second portions, each of the first and second portions including at least one loop, and an intermediate portion in communication with the first and second portions, each of the at least one loop of each of the first and second portions including oppositely disposed blunt ends facing each other and being elastically deformable to change shape to collapse upon itself and assume the contour of the teeth to provide a maximum surface area of the respective first and second portion for contact with teeth, when the intermediate portion is moved within the inter-proximal space between adjacent teeth, each of the first and second portions sized to remain on its respective side of the adjacent teeth.

8. The dental apparatus of claim 7, additionally comprising: a gripping portion in communication with at least one of the oppositely disposed first and second portions.

9. The dental apparatus of claim 7, wherein the first and second portions include fibers.

10. The dental apparatus of claim 7, wherein at least one of the first and second portions includes a therapeutic substance.

* * * * *